US007842279B2

(12) United States Patent
McBride et al.

(10) Patent No.: US 7,842,279 B2
(45) Date of Patent: Nov. 30, 2010

(54) F-18 PEPTIDES FOR PRE TARGETED POSITRON EMISSION TOMOGRAPHY IMAGING

(75) Inventors: William J. McBride, Boonton, NJ (US); Carl F. Noren, Elizabeth, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 957 days.

(21) Appl. No.: 11/500,774

(22) Filed: Aug. 8, 2006

(65) Prior Publication Data

US 2007/0048217 A1 Mar. 1, 2007

Related U.S. Application Data

(60) Provisional application No. 60/712,433, filed on Aug. 31, 2005.

(51) Int. Cl.
A61K 51/00 (2006.01)
A61M 36/14 (2006.01)
(52) U.S. Cl. .................. 424/1.89; 424/1.11; 424/1.65; 424/1.69; 424/1.81; 424/1.185
(58) Field of Classification Search ............... 424/1.11, 424/1.65, 1.81, 1.85, 1.89, 9.1, 9.3, 9.4, 9.5, 424/9.6, 9.7, 9.8; 530/300, 333, 334, 335, 530/336, 337, 338, 339, 342, 343, 350
See application file for complete search history.

(56) References Cited

U.S. PATENT DOCUMENTS

| | | | |
|---|---|---|---|
| 5,446,147 A | 8/1995 | Kung et al. | |
| 6,056,939 A | 5/2000 | Desreux et al. | |
| 6,207,858 B1 | 3/2001 | Chinn et al. | |
| 7,563,433 B2 * | 7/2009 | McBride et al. | ............ 424/1.89 |
| 7,597,876 B2 * | 10/2009 | McBride et al. | ............ 424/1.89 |
| 2001/0056096 A1 | 12/2001 | Medina et al. | |

FOREIGN PATENT DOCUMENTS

WO 9816254 4/1998

OTHER PUBLICATIONS

Chesis et al., "Comparison of Bromo-and Iodoalkyl Triflates for 18F-Radiolabeling of Amines", Appl. Radiat. Isot., vol. 41(3):259-265, 1990.
Choe et al., "[18 F]Fluoromethylbenzylsulfonate Ester: a Rapid and Efficient Synthetic Method for the N-[18F] Fluoromethylbenzylation of Amides and Amines", Appl. Radiat. Isot., vol. 49(1-2):73-77, 1998.
Choi et al., "Biodistribution of 18F-and 125I-labeled Anti-Tac Disulfide-stabilized Fv Fragments in Nude Mice with Interleukin 2a Receptor-positive Tumor Xenografts", Cancer Research 55, pp. 5323-5329, 1995.
Downer et al., "Reactivity of p-[18F]Fluorophenacyl Bromide for Radiolabeling Of Proteins and Peptides", Appl. Radiat. Isot., vol. 48(7):907-916, 1997.
Garg et al., "Fluorine-18 Labeling of Monoclonal Antibodies and Fragments with Preservation of Immunoreactivity", Bioconjugate Chem., vol. 2:44-49, 1991.
Gray et al., "Antibodies to Carbohydrates: Preparation of Antigens by Coupling Carbohydrates to Proteins by Reductive Amination with Cyanoborohydride", Methods Enzymol. 1978;50:155-60.
Herman et al., "The Use of Pentafluorophenyl Derivatives for the 18F Labelling of Proteins", Nucl. Med. Biol., vol. 21 (7):1005-1010, 1994.
Hudlicky, M., "Methods for Introducing Fluorine and Replacement of Halogens by Fluorine", Chemistry of Organic Fluorine Compounds, John Wiley and Sons, Publ., NY 1976, pp. 112-129.
Iwata et al., "A new, convenient method for the preparation of 4-[18F]fluorobenzyl halides", Appl. Radiat. Isot. Jan. 2000;52(1):87-92.
Jacobson et al., "A Prosthetic Group for the Rapid Introduction of Fluorine Into Peptides and Functionalized Drugs", Journal of Florine Chemistry, vol. 39:339-347, 1988.
Kilbourn et al., "Fluorine-18 Labeling of Proteins", J. Nucl. Med., vol. 28(4):462-470, 1987.
Lang et al., "One-Step Synthesis of 18F Labeled (18F)-N-succinimidyl 4-(fluoromethyl)benzoate for Protein Labeling", Appl. Radiat. Isot, vol. 45(12):115-1163, 1994.
Page et al., "Preclinical Evaluation and PET Imaging of 18F-labeled Mel-14 F(ab')2 Fragment in Normal Dogs", Nucl. Med. Biol., vol. 21(7):911-919, 1994.
Poethko et al., "Two-Step Methodology for High-Yield Routine Radiohalogenation of Peptides: 18F-Labeled RGD and Octreotide Analogs", J. Nucl. Med. May 2004;45(5):892-902.
Schottelius et al., "First (18)F-Labeled Tracer Suitable for Routine Clinical Imaging of sst Receptor-Expressing Tumors Using Positron Emission Tomography", Clin. Cancer Res. Jun. 1, 2004;10(11):3593-606.
Sheppard et al., "Classical Methods of Fluorination", Organic Fluorine Chemistry, W.A. Benjamin and Comp., Publ., New York, 1969, pp. 82-91.
Shiue et al., "Synthesis of 18F-Labelled N-(p-[18F]fluorophenyl)maleimide and Its Derivatives for Labelling Monoclonal Antibody With 18F", J. Labelled Compd. Radiopharm., vol. 26:287-289, 1989.
Sykes et al., "Synthesis and Murine Tissue Uptake of Sodium [18F]Fluoroacetate", Nucl. Med. Biol., vol. 13 (5):497-500, 1986.
Vaidyanathan et al., "Fluorine-18-Labeled [Nle4,D-Phe7]-α-MSH, an α-Melanocyte Stimulating Hormone Analogue", Nucl. Med. Biol., vol. 24:171-178, 1997.
Vaidyanathan et al., "Fluorine-18-Labeled Monoclonal Antibody Fragments: A Potential Approach for Combining Radioimmunoscintigraphy and Positron Emission Tomography", J. Nucl. Med., vol. 33(8):1535-1541, 1992.
Vaidyanathan et al., "Improved Synthesis of N-Succinimidyl 4[18F]Fluorobenzoate and Its Application to the Labeling Of a Monoclonal Antibody Fragment", Bioconjugate Chem., vol. 5:352-356, 1994.

(Continued)

*Primary Examiner*—D L Jones
(74) *Attorney, Agent, or Firm*—Richard A. Nakashima

(57) ABSTRACT

F-18 radiolabeled peptides are prepared by reacting a peptide comprising a hydroxylamine, a thiosemicarbazide, a hydrazine or a free amine group with 4-[$^{18}$F]Fluorobenzaldehyde. Specific, non-limiting examples of F-18 radiolabeled peptides are described herein. The labeled peptides are useful, for example, in clinical positron emission tomography.

11 Claims, 5 Drawing Sheets

OTHER PUBLICATIONS

Vaidyanathan et al., "Fluorine-18 Labeled Chemotactic Peptides: A Potential Approach for the PET Imaging of Bacterial Infection", Nucl. Med. Biol., vol. 22(6):759-764, 1995.

Wilbur, "Radiohalogenation of Proteins: An Overview of Radionuclides, Labeling Methods, and Reagents for Conjugate Labeling", Bioconjugate Chem., vol. 3(6):433-470, 1992.

Wilson et al., "Synthesis of Two Radiofluorinated Cocaine Analogues Using Distilled 2-[18F]Fluoroethyl Bromide", Appl. Radiat. Isot., vol. 46(8):765-770, 1995.

Wilson et al., "Reductive Amination of [18F]Fluorobenzaldehydes: Radiosyntheses of [2-18F]- and [4-18F] Fluorodexetimides", J. Labelled Compd. Radiopharm., vol. 28(10):1189-1199, 2006.

Zalutsky et al., "Fluorine-18-Antimyoshin Monoclonal Antibody Fragments: Preliminary Investigations in a Canine Myocardial Infarct Model", J. Nucl. Med., Vol. 33(4):575-580, 1992.

Zheng et al., "Synthesis Of Fluorine-18 Labeled Fluoromethyl Iodide, A Synthetic Precursor for Fluoromethylation of Radiopharmaceuticals",J. Nucl. Med., Abstract No. 761, vol. 38(5):177P, 1997.

* cited by examiner

F-18 PEPTIDES FOR PRE TARGETED POSITRON EMISSION TOMOGRAPHY IMAGING

RELATED APPLICATIONS

The present application claims the benefit under 35 U.S.C. § 119(e) of provisional U.S. Patent Application Ser. No. 60/712,433, filed Aug. 31, 2005, and the PCT application entitled "F-18 PEPTIDES FOR PRETARGETED POSITRON EMISSION TOMOGRAPHY IMAGING" PCT/US06/30992, filed Aug. 8, 2006, incorporated herein by reference.

FIELD OF THE INVENTION

Various embodiments of the present invention concern methods and compositions for radiolabeling peptides with $^{18}$F. In particular embodiments, $^{18}$F-labeled peptides are of use for various diagnostic applications, such as positron emission tomography (PET). Even more particular embodiments concern compositions and methods of use of [$^{18}$F]Fluorobenzaldehyde for $^{18}$F labeling of peptides.

BACKGROUND OF THE INVENTION

Positron emission tomography (PET) is a high resolution, non-invasive, imaging technique for the visualization of human disease. In PET, 511 keV gamma photons produced during positron annihilation decay are detected. In the clinical setting, fluorine-18 (F-18) is one of the most widely used positron-emitting nuclides. F-18 has a half-life ($t_{1/2}$) of 110 minutes, and emits β+ particles at an energy of 635 keV. It is 97% abundant.

The short half-life of F-18 has limited or precluded its use with longer-lived specific targeting vectors such as antibodies, antibody fragments, recombinant antibody constructs and longer-lived receptor-targeted peptides. In addition, complicated chemistry has been required to link the inorganic fluoride species to such organic targeting vectors. In typical synthesis methods, an intermediate is radiofluorinated, and the F-18-labeled intermediate is purified for coupling to protein amino groups. See, e.g., Lang et al., Appl. Radiat. Isol., 45 (12): 1155-63 (1994); Vaidyanathan et al., Bioconj. Chem., 5: 352-56 (1994).

These methods are tedious to perform and require the efforts of specialized professional chemists. They are not amenable to kit formulations for use in a clinical setting. Multiple purifications of intermediates are commonly required, and the final step, involving linkage to protein lysine residues, usually results in 30-60% yields, necessitating a further purification step prior to patient administration. In addition, these methods result in fluorinated targeting species which accumulate in the kidney, somewhat like radiometals.

As discussed above, the currently available methods for labeling protein-based targeting vectors with F-18 are unsuitable. There is a need, therefore, for a simple, efficient method for incorporating the F-18 radionuclide into peptide-containing targeting vectors, such as proteins, antibodies, antibody fragments, and receptor-targeted peptides, to allow the use of such targeting vectors in routine clinical positron emission tomography.

SUMMARY OF THE INVENTION

The present invention provides improved methods and compositions for incorporating the F-18 radionuclide into a peptide sequence. In various aspects, the methods and compositions may provide for improved efficiency of F-18 incorporation, decreased need for purification steps after peptide radiolabeling, and/or greater simplicity and ease of use of F-18 radiolabeling compared to previously known methods. Although preferred embodiments concern F-18 labeling of peptides that may then be non-covalently attached to a targeting vector, for example by pre-targeting methods discussed below, in alternative embodiments an F-18 label may be covalently attached directly to a targeting vector, for example by use of [$^{18}$F]Fluorobenzaldehyde and a hydroxylamine, thiosemicarbazide or hydrazine under conditions that promote formation of an oxime, thiosemicarbozone or hydrazone, or in other alternatives by use of a $^{18}$F-labeled aldehyde bisulfite addition complex and reductive amination.

In accordance with one embodiment of the invention, there is provided a method wherein a peptide sequence comprising at least one HSG, DTPA or DOTA group and at least one group selected from either a hydroxylamine, a thiosemicarbazide or a hydrazine is treated with 4-[$^{18}$F]Fluorobenzaldehyde under conditions that promote the formation of the corresponding oxime, thiosemicarbazone or hydrazone.

In accordance with another embodiment of the invention, there is provided a method for generating the 4-[$^{18}$F]Fluorobenzaldehyde in situ by the acid-catalyzed decomposition of the addition complex of 4-[$^{18}$F]Fluorobenzaldehyde and sodium bisulfite.

Still other embodiments provide a peptide having the sequence 4-$^{18}$F—$C_6H_4$CH=NR-A-Lys(X)-B-Lys(X), wherein R is selected from a group consisting of —O—$CH_2$—CO—, —NH—CS—NH—$C_6H_4$—CO—, and —NH—$C_6H_4$—CO—, A is (Tyr)$_n$, wherein n=0 or 1, X is independently selected from a group consisting of HSG, DTPA, and DOTA, and B is selected from a group consisting of Glu, Ala, and Tyr.

BRIEF DESCRIPTION OF THE DRAWINGS

Scheme 1: Conjugation of 4-[$^{18}$F]Fluorobenzaldehyde to Peptide Via Oxime Linker Scheme 2: Conjugation of 4-[$^{18}$F]Fluorobenzaldehyde to Peptide Via Thiosemicarbazone Linker Scheme 3: Conjugation of 4-[$^{18}$F]Fluorobenzaldehyde to Peptide Via Hydrazone Linker Scheme 4: Concentration of 4-[$^{18}$F]Fluorobenzaldehyde by Formation of Bisulfite Addition Complex: α-Hydroxy-4-[$^{18}$F]Fluoro-α-toluenesulfonic Acid FIG. 1. Analysis of 4-[$^{18}$F]Fluorobenzaldehyde By Reverse Phase HPLC. The change in baseline at 20 min was due to movement of samples in the carousel of the auto injector.

DETAILED DESCRIPTION OF THE INVENTION

Figure 1:
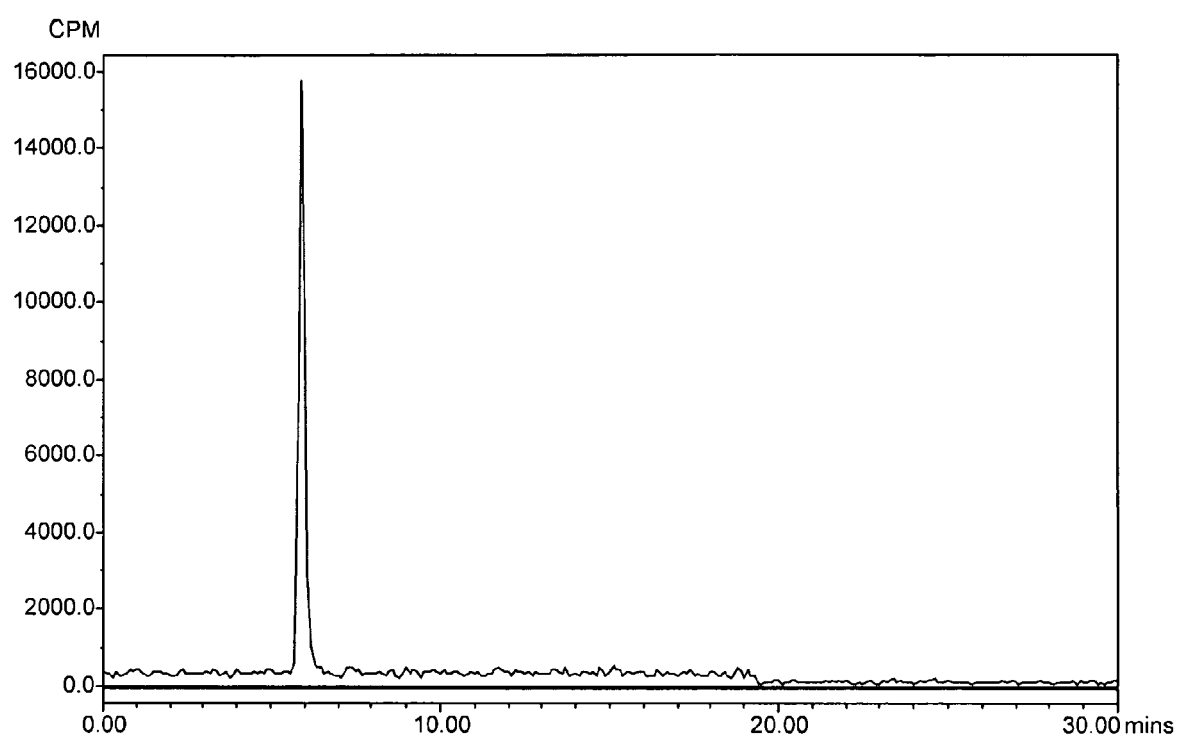

As used herein, "a" or "an" may mean one or more than one of an item.

As used herein, the terms "and" and "or" may be used to mean either the conjunctive or disjunctive. That is, both terms should be understood as equivalent to "and/or" unless otherwise stated.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion or analog of an immunoglobulin molecule, like an antibody fragment.

An antibody fragment is a portion of an antibody such as $F(ab)_2$, $F(ab')_2$, Fab, Fv, sFv and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units (CDR) consisting of the amino acid residues that mimic the hypervariable region.

As used herein, the term antibody fusion protein refers to a recombinantly produced antigen-binding molecule in which two or more of the same or different scFv or antibody fragments with the same or different specificities are linked. Valency of the fusion protein indicates how many binding arms or sites the fusion protein has to a single antigen or epitope; i.e., monovalent, bivalent, trivalent or multivalent. The multivalency of the antibody fusion protein means that it can take advantage of multiple interactions in binding to an antigen, thus increasing the avidity of binding to the antigen. Specificity indicates how many antigens or epitopes an antibody fusion protein is able to bind; i.e., monospecific, bispecific, trispecific, multispecific. Using these definitions, a natural antibody, e.g., an IgG, is bivalent because it has two binding arms but is monospecific because it binds to one epitope. Monospecific, multivalent fusion proteins have more than one binding site for an epitope but only binds to one such epitope, for example a diabody with two binding site reactive with the same antigen. The fusion protein may comprise a single antibody component, a multivalent or multispecific combination of different antibody components, or multiple copies of the same antibody component. The fusion protein may additionally comprise an antibody or an antibody fragment and a therapeutic agent. Examples of therapeutic agents suitable for such fusion proteins include immunomodulators ("antibody-immunomodulator fusion protein") and toxins ("antibody-toxin fusion protein").

Overview

The present invention provides simple and efficient methods for incorporating an F-18 radionuclide into peptide or protein sequences, using an $^{18}$F-labeled aldehyde. The disclosed methods and compositions makes such peptide or protein sequences available for routine clinical positron emission tomography.

The claimed methods and compositions take advantage of the property of aldehydes to rapidly and selectively undergo reaction with groups such as hydroxylamines, thiosemicarbazides and hydrazines to form the corresponding oximes, thiosemicarbazones and hydrazones, respectively. This reaction can occur in the presence of other nucleophilic groups such as side chain amino groups of lysine residues, for example. The $^{18}$F label is incorporated into the aldehyde and is therefore incorporated into the peptide upon formation of the covalent bond between the aldehyde and the peptide. The invention further provides a convenient method of handling the labeled aldehydes, which can be volatile, by forming the bisulfite addition complex of the aldehyde and using the complex in situ to form the oximes, thiosemicarbazones or hydrazones.

In a particular embodiment, the aldehyde used is 4-Fluorobenzaldehyde, which can be prepared in F-18 form by displacement of a leaving group, using labeled fluoride ion, by known methods.

The methods are particularly amenable to the labeling of synthetically produced peptides, which can be modified during synthesis to contain a nucleophilic hydroxylamine, thiosemicarbazide or hydrazine moiety that can be used to react with the labeled aldehyde. The methods can be used for any peptide sequence of interest that can accommodate a suitable nucleophilic moiety. Typically the nucleophilic moiety is appended to the N-terminus of the peptide, but the skilled artisan will recognize that the nucleophile also can be linked to an amino acid side chain or to the peptide C-terminus.

The methods of the present invention are particularly suitable for, though not limited to, labeling peptides for use in affinity enhancement systems that use a bispecific or multispecific antibody. In these methods, the antibody has a first specificity to a target tissue and a second specificity to a targetable construct. See, for example, US20030198595, which is incorporated herein by reference in its entirety. In an imaging application, the antibody typically is first administered to a subject, followed by a period of time to allow unbound antibody to clear. The detectably labeled targetable construct is then administered and is sequestered at sites at which the antibody is bound, permitting detection of the complex. In certain embodiments, $^{18}$F-labeled peptides may be prepared that function as targetable constructs for binding to bispecific or multispecific antibodies. The skilled artisan will be aware that other administration regimens are possible.

In a particular embodiment of the invention, the methods can be used to prepare labeled peptides bearing haptenic moieties such as HSG (histaminyl-succinyl-glycyl—see US20030198595) or a chelator such as diethylenetriamine pentaacetic acid (DTPA) or 1,4,7,10-tetraazacyclododecane N,N',N'',N'''tetraacetic acid (DOTA) or their metal complexes. DTPA and DOTA-type chelators, where the ligand includes hard base chelating functions such as carboxylate or amine groups, are most effective for chelating hard acid cations, especially Group IIa and Group IIIa metal cations such as Ga and In. Other suitable metals include but are not limited to transition metals and inner transition metals such as Y and Lu. Such metal-chelate complexes can be made very stable by tailoring the ring size to the metal of interest. For example, the labeled peptide can have the formula:

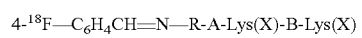

where R may be, for example, —O—CH$_2$—CO, —NH—CS—NH—C$_6$H$_4$—CO—, and —NH—C$_6$H$_4$—CO—. A is (Tyr)$_n$, and n=0 or 1. X can be a hapten group such as HSG, or X is a chelator, and B is selected from the group consisting of Glu, Ala, and Tyr.

The invention also provides methods of radiolabeling essentially any molecule that contains a moiety comprising a nucleophilic nitrogen atom capable of forming a nitrogen-carbon double bond, for example any moiety containing a primary amine, a secondary amine, a hydroxylamine, a thiosemicarbazide or a hydrazine. The molecule is contacted with the bisulfite addition complex of [$^{18}$F]Fluorobenzaldehyde under conditions that promote the formation of a double bond between the nucleophilic nitrogen atom and the aldehyde. The reaction can be performed in the presence of a reducing agent such that the double bond is reduced in situ. When the nucleophile is a secondary amine the reaction is preferably carried out in the presence of a reducing agent.

Method of Formation

Methods of synthesizing a radiolabeled peptide sequence are provided in which 4-[$^{18}$F]Fluorobenzaldehyde is reacted with a peptide sequence comprising either a hydroxylamine, a thiosemicarbazide or a hydrazine group, thereby forming the corresponding oximes, thiosemicarbazones or hydrazones, respectively. The 4-[$^{18}$F]Fluorobenzaldehyde typically is generated in situ by the acid-catalyzed decomposition of the addition complex of 4-[$^{18}$F]Fluorobenzaldehyde and sodium bisulfite. The use of the bisulfite addition complex enhances the speed of purification since, unlike the aldehyde, the complex can be concentrated to dryness. Formation of the complex is also reversible under acidic and basic conditions. In particular, when the complex is contacted with a peptide containing a hydroxylamine, a thiosemicarbazide or a hydrazine group in acidic medium, the reactive free 4-[$^{18}$F]Fluorobenzaldehyde is consumed as it is formed in situ, resulting in the corresponding F-18 radiolabeled peptide sequence.

In the instances when the oxime, thiosemicarbazone or hydrazone linkages present in vivo instability, an additional reduction step may be employed to reduce the double bond connecting the peptide to the F-18 bearing substrate. The corresponding reduced peptide linkage would enhance the stability. One skilled in the art would appreciate the variety of methods available to carry out such a reduction step. Reductive amination steps as described in Wilson et al., Journal of Labeled Compounds and Radiopharmaceuticals, XXVIII (10), 1189-1199, 1990 may also be used to form a Schiff's base involving a peptide and 4-[$^{18}$F]Fluorobenzaldehyde and directly reducing the Schiff's base using reducing agents such as sodium cyanoborohydride.

The 4-[$^{18}$F]Fluorobenzaldehyde may be prepared as described in Wilson et al., Journal of Labeled Compounds and Radiopharmaceuticals, XXVIII (10), 1189-1199, 1990; Iwata et al., Applied radiation and isotopes, 52, 87-92, 2000; Poethko et al., The Journal of Nuclear Medicine, 45, 892-902, 2004; and Schottelius et al., Clinical Cancer Research, 10, 3593-3606, 2004. The Na$^{18}$F in water may be added to a mixture of kryptofix and K$_2$CO$_3$. Anhydrous acetonitrile may be added and the solution is evaporated in a heating block under a stream of argon. Additional portions of acetonitrile may be added and evaporated to completely dry the sample. The 4-trimethylammoniumbenzaldehyde triflate may be dissolved in DMSO and added to the dried F-18. The solution may then be heated in the heating block. The solution may be cooled briefly, diluted with water and filtered through a Waters® Oasis HLB LP extraction cartridge. The cartridge may be washed with 9:1 water:acetonitrile and water to remove unbound F-18 and unreacted 4-trimethylammonium-benzaldehyde triflate. The 4-[$^{18}$F]Fluorobenzaldehyde may then be eluted from the cartridge with methanol in fractions (HPLC, FIG. 1).

Method of Administration

It should be noted that much of the discussion presented herein below focuses on the use of F-18 radiolabeled peptide or protein sequences in the context of imaging diseased tissue. The claimed methods also contemplate, however, the use of F-18 radiolabeled peptide or protein sequences in imaging normal tissue and organs using the methods described, for example, in U.S. Pat. Nos. 6,126,916; 6,077,499; 6,010,680; 5,776,095; 5,776,094; 5,776,093; 5,772,981; 5,753,206; 5,746,996; 5,697,902; 5,328,679; 5,128,119; 5,101,827; and 4,735,210, the contents of each of which are hereby incorporated by reference in their entireties. As used herein, the term "tissue" refers to tissues, including but not limited to, tissues from the pancreas, ovary, thymus, parathyroid or spleen.

The administration of a bispecific antibody ("bsAb") and a labeled targetable construct may be conducted by administering the bsAb at some time prior to administration of the targetable construct. The doses and timing of the reagents can be readily devised by a skilled artisan, and are dependent on the specific nature of the reagents employed. If a bsAb-F(ab')$_2$ derivative is given first, then typically a waiting time of 6-73 hr, preferably 24-48 hr, before administration of the targetable construct is appropriate. If an IgG-Fab' bsAb conjugate is the primary targeting vector, then a longer waiting period before administration of the targetable construct may be indicated, in the range of 3-19 days.

After sufficient time has passed for the bsAb to target to the diseased tissue, the $^{18}$F-labeled targetable construct is administered. Subsequent to administration of the diagnostic agent, imaging can be performed using PET. PET is a high resolution, non-invasive, imaging technique can be used for the visualization of diseased or normal human tissue. In PET, 511 keV gamma photons produced during positron annihilation decay are detected.

The claimed methods and compositions also contemplate the use of multivalent target binding proteins which have at least three different target binding sites as described in Patent Appl. Publication No. 20020076406, incorporated herein by reference. Multivalent target binding proteins have been made by cross-linking several Fab-like fragments via chemical linkers. See U.S. Pat. Nos. 5,262,524; 5,091,542 and Landsdorp et al., Euro. J. Immunol. 16: 679-83 (1986). Multivalent target binding proteins also have been made by covalently linking several single chain Fv molecules (scFv) to form a single polypeptide. See U.S. Pat. No. 5,892,020. A multivalent target binding protein which is basically an aggregate of scFv molecules has been disclosed in U.S. Pat. Nos. 6,025,165 and 5,837,242. A irivalent target binding protein comprising three scFv molecules has been disclosed in Krott et al., Protein Engineering 10(4): 423-433 (1997).

A clearing agent may be used which is given between doses of the bsAb and the linker moiety. A suitable clearing agent is a glycosylated anti-idiotypic Fab' fragment targeted against the disease targeting arm(s) of the bsAb. For, example, anti-CEA (MN 14 Ab)×anti-targetable construct bsAb is given and allowed to accrete in disease targets to its maximum extent. To clear residual bsAb, an anti-idiotypic Ab to MN-14, termed WI2, is given, preferably as a glycosylated Fab' fragment. The clearing agent binds to the bsAb in a monovalent manner, while its appended glycosyl residues direct the entire complex to the liver, where rapid metabolism takes place. Then the targetable construct that binds to the second arm of the bsAb is given to the subject. The WI2 Ab to the MN-14 arm of the bsAb has a high affinity and the clearance mechanism differs from other disclosed mechanisms (see Goodwin et al., ibid), as it does not involve cross-linking, because the WI2-Fab' is a monovalent moiety.

Antibodies

Various embodiments may concern antibodies and/or antibody fragments expressed from the transfected cell lines of interest. The term "antibody" is used herein to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlowe and Lane, 1988, *Antibodies. A Laboratory Manual*, Cold Spring Harbor Laboratory). Antibodies of use may also be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and are available for use in the claimed methods and compositions. (See, for example, U.S. Pat. Nos. 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,652,852; 6,635,482; 6,630,144; 6,610,833; 6,610,294; 6,605,441; 6,605,279; 6,596,852; 6,592,868; 6,576,745; 6,572;856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206; 6,441,143; 6,432,404; 6,432,402; 6,419,928; 6,413,726; 6,406,694; 6,403,770; 6,403,091; 6,395,274; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459 each incorporated herein by reference with respect to the ATCC deposit number for the antibody-secreting hybridoma cell lines and the associated target antigens for the antibodies or fragments thereof.) These are exemplary only and a wide variety of other antibody-secreting hybridomas are known in the art. The skilled artisan will realize that antibody-secreting hybridomas against almost any disease-associated antigen may be obtained by a simple search of the ATCC, PubMed and/or USPTO databases for antibodies against a selected disease-associated target of interest. The antigen binding domains of the cloned antibodies may be amplified, excised, ligated into an expression vector, transformed into an adapted host cell and used for protein production, using standard techniques well known in the art.

Production of Antibody Fragments

Some embodiments of the claimed methods and/or compositions may concern antibody fragments. Exemplary methods for producing antibody fragments are disclosed in U.S. Pat. No. 4,036,945; U.S. Pat. No. 4,331,647; Nisonoff et al., 1960, Arch. Biochem. Biophys., 89:230; Porter, 1959, Biochem. J., 73:119; Edelman et al., 1967, METHODS IN ENZYMOLOGY, page 422 (Academic Press), and Coligan et al. (eds.), 1991, CURRENT PROTOCOLS IN IMMUNOLOGY, (John Wiley & Sons).

Other methods of forming antibody fragments, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, Proc. Nat'l. Acad. Sci. USA, 69:2659. Alternatively, the variable chains may be linked by an intermolecular disulfide bond or cross-linked by chemicals such as glutaraldehyde. See Sandhu, 1992, Crit. Rev. Biotech., 12:437.

Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell. The recombinant host cells synthesize a single polypeptide chain with a linker peptide bridging the two V domains. Methods for producing sFv's are well-known in the art. See Whitlow et al., 1991, Methods: A Companion to Methods in Enzymology 2:97; Bird et al., 1988, Science, 242:423; U.S. Pat. No. 4,946, 778; Pack et al., 1993, Bio/Technology, 11:1271, and Sandhu, 1992, Crit. Rev. Biotech., 12:437.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, Methods: A Companion to Methods in Enzymology 2:106; Ritter et al. (eds.), 1995, MONOCLONAL ANTIBODIES: PRODUCTION, ENGINEERING AND CLINICAL APPLICATION, pages 166-179 (Cambridge University Press); Birch et al., (eds.), 1995, MONOCLONAL ANTIBODIES: PRINCIPLES AND APPLICATIONS, pages 137-185 (Wiley-Liss, Inc.). Where an antibody-secreting hybridoma cell line is publicly available, the CDR sequences encoding antigen-binding specificity may be obtained, incorporated into chimeric or humanized antibodies, and used. As discussed above, such antibodies or antibody fragments may be designed, for example, as bispecific or multispecific targeting vectors, with at least one binding site directed towards a tissue-specific or tissue-selective target antigen and at least one other binding site directed towards an F-18 labeled peptide. Alternatively, antibodies, fusion proteins or fragments thereof may be directly labeled with F-18 as discussed below. The skilled artisan will realize that the targeting vectors of use are not limited to antibodies, fusion proteins or fragments thereof, but may also utilize any other known type of targeting vector, such as aptamers (e.g., U.S. Pat. Nos. 5,270,163; 5,567,588; 5,650,275; 5,670,637; 5,683,867; 5,696,249; 5,789,157; 5,843,653; 5,864,026; 5,989,823), avimers (e.g., Silverman et al., Nature Biotechnol. 23:1556-61, 2005) or affibodies (e.g., U.S. Pat. No. 5,831,012).

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. The affinity of humanized antibodies for a target may also be increased by selected modification of the CDR sequences (WO0029584A1). Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immunol., 1993, 150:2844.)

Other embodiments may concern non-human primate antibodies. General techniques for raising therapeutically useful antibodies in baboons may be found, for example, in Goldenberg et al., WO 91/11465 (1991), and in Losman et al., Int. J. Cancer 46: 310 (1990).

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods, as known in the art. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols. A non-limiting example of such a system is the XenoMouse® (e.g., Green et al., 1999, *J. Immunol. Methods* 231:11-23, incorporated herein by reference) from Abgenix (Fremont, Calif.). In the XenoMouses and similar animals, the mouse antibody genes have been inactivated and replaced by functional human antibody genes, while the remainder of the mouse immune system remains intact.

The XenoMouse® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XenoMouse® immunized with a target antigen will produce human antibodies by the normal immune response, which may be harvested and/or produced by standard techniques discussed above. A variety of strains of XenoMouse® are available, each of which is capable of producing a different class of antibody. Such human antibodies may be coupled to other molecules by chemical cross-linking or other known methodologies. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XenoMouse® system but may utilize any transgenic animal that has been genetically engineered to produce human antibodies.

EXAMPLES

The embodiments of the invention are further illustrated through examples which show aspects of the invention in detail. These examples illustrate specific elements of the invention and are not to be construed as limiting the scope thereof.

1) IMP 286 Conjugation (Scheme 1)

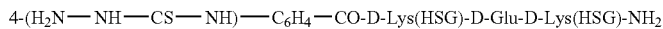

IMP 286 MH⁺ 1097

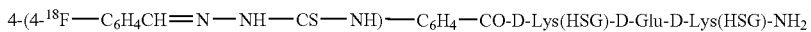

10

The peptide, IMP 286 (MH⁺1097), 0.0024 g ($2.19 \times 10^{-6}$ mol) was dissolved in 729 µL of 0.1% TFA in water. The 4-[$^{18}$F]Fluorobenzaldehyde was prepared as described above. A 200 µL fraction of the methanol solution of 4-[$^{18}$F] Fluorobenzaldehyde was mixed with 200 µL of the IMP 286 solution. The reaction was heated in a 100° C. heating block for 16 min. The HPLC analysis of the crude reaction product showed that the reaction had gone 50% to the peptide conjugate.

2) IMP 316 Conjugation (Scheme 2)

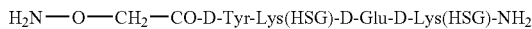

IMP 316 MH⁺ 1140

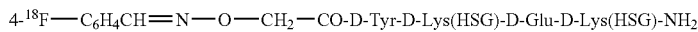

30

Figure 2:
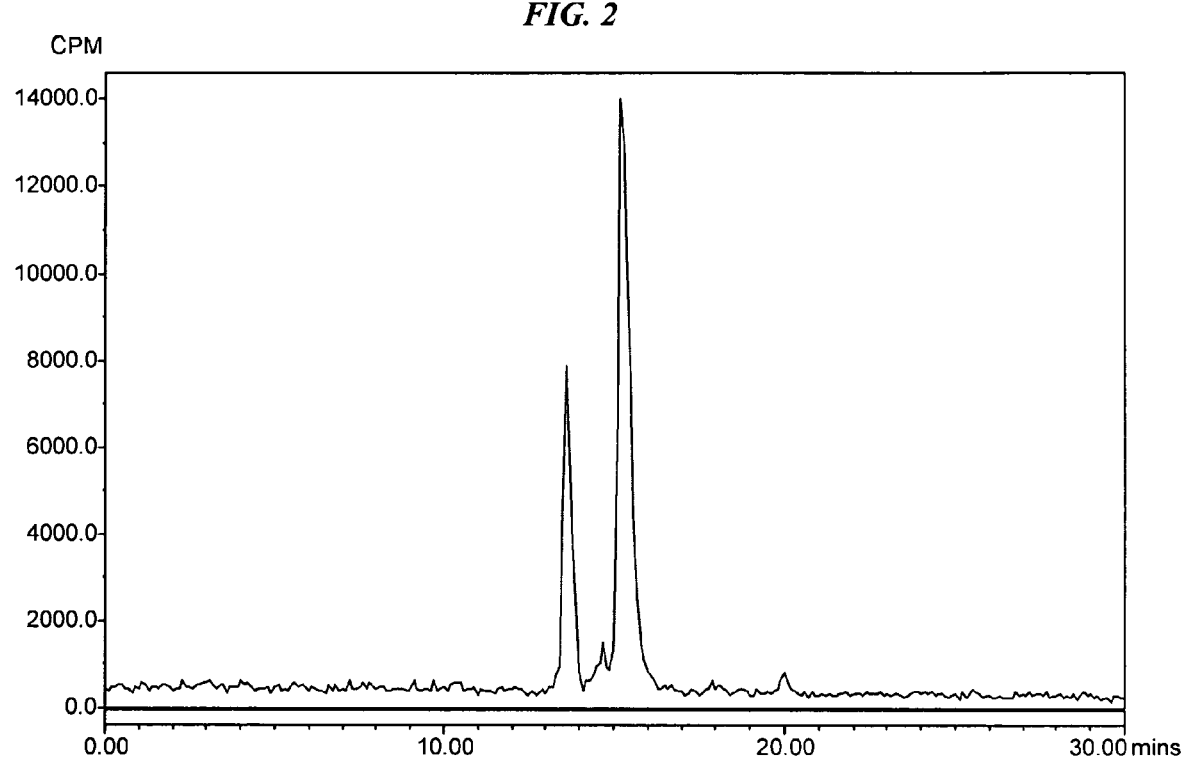
FIG. 2. Analysis of IMP 316 Peptide Conjugation Reaction via Oxime Linkage by Reverse Phase HPLC and Radiometric Detection.
Figure 3:
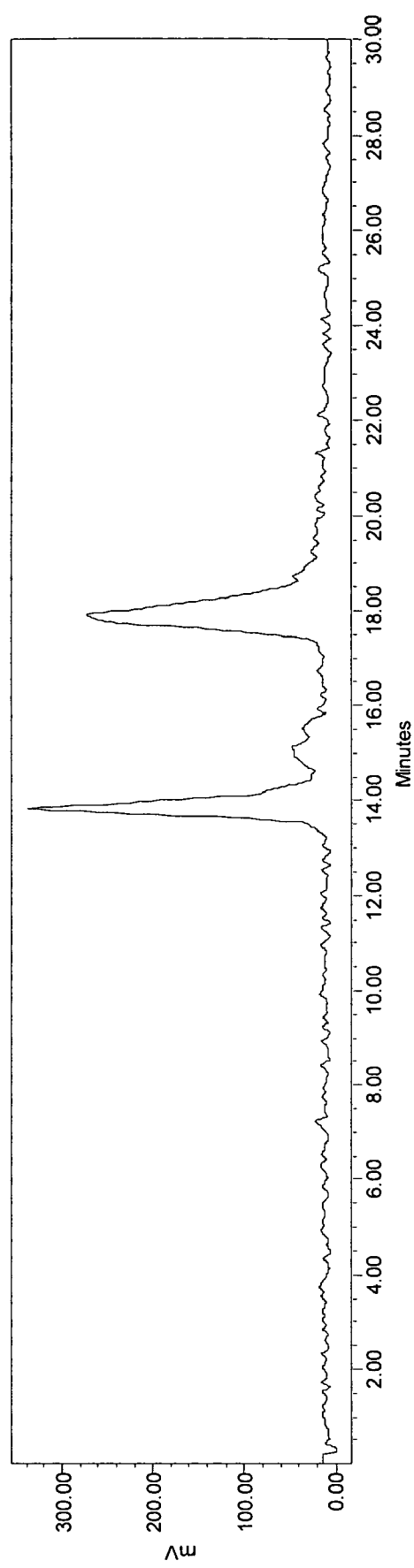
FIG. 3. Analysis of IMP 316 Peptide Conjugation Reaction Products by Size Exclusion HPLC and Radiometric Detection.
Figure 4:
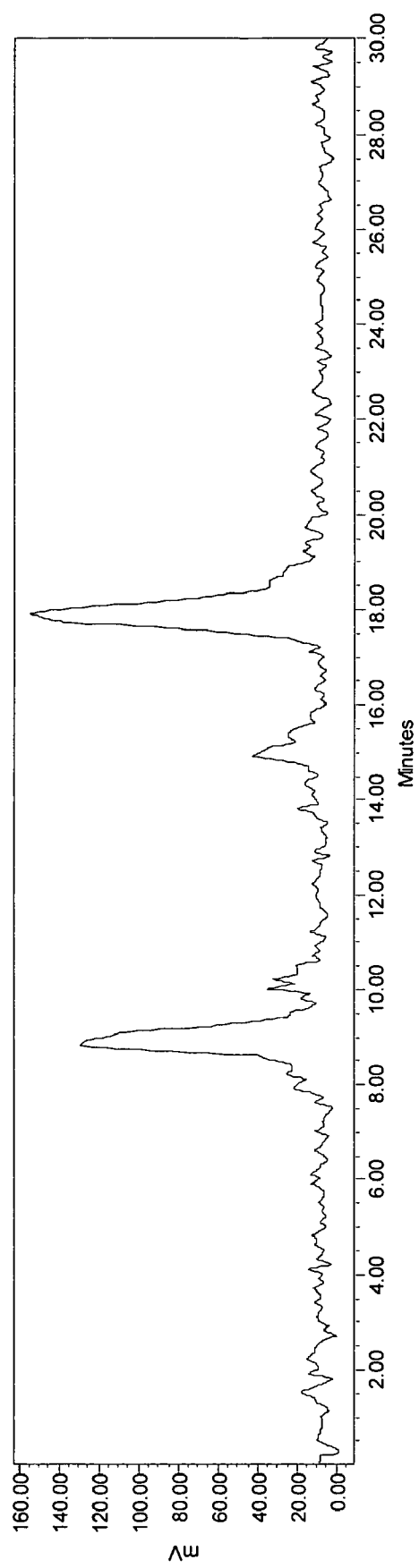
FIG. 4. Analysis of IMP 316 Peptide Conjugation Products Mixed With hMN-14×679 by Size Exclusion HPLC and Radiometric Detection.

The peptide, IMP 316 (MH⁺ 1140), 0.0025 g ($2.19 \times 10^{-6}$ mol) was dissolved in 365 µL of 0.5 M AcOH in water ($6 \times 10^{-3}$M). The 4-[$^{18}$F]Fluorobenzaldehyde was prepared as described above and eluted from an Oasis HLB cartridge in methanol. A 1 mL fraction of the methanol solution of 4-[$^{18}$F] Fluorobenzaldehyde was mixed with 50 µL of the IMP 316 solution. The reaction was heated in a 100° C. heating block for 13 min, then the solution was concentrated (100° C.) under a stream of argon for 6 min. The reverse phase HPLC analysis (Waters Xterra® Column, 0.1% TFA/CH₃CN buffers, FIG. 2) of the crude reaction product showed that the reaction had gone ~30-40% to the peptide conjugate with a specific activity of ~1 Ci/mmol as the reaction was done. The size exclusion HPLC (Bio Rad, Biosil Column, phosphate buffers, FIG. 3 and FIG. 4) demonstrated that the new product formed showed binding to the bispecific antibody hMN-14× 679 which indicated that the F-18 was conjugated to the peptide.

3) α-Hydroxy-4-[$^{18}$F]-Fluoro-α-toluenesulfonic Acid Preparation (Scheme 3)

Figure 5:
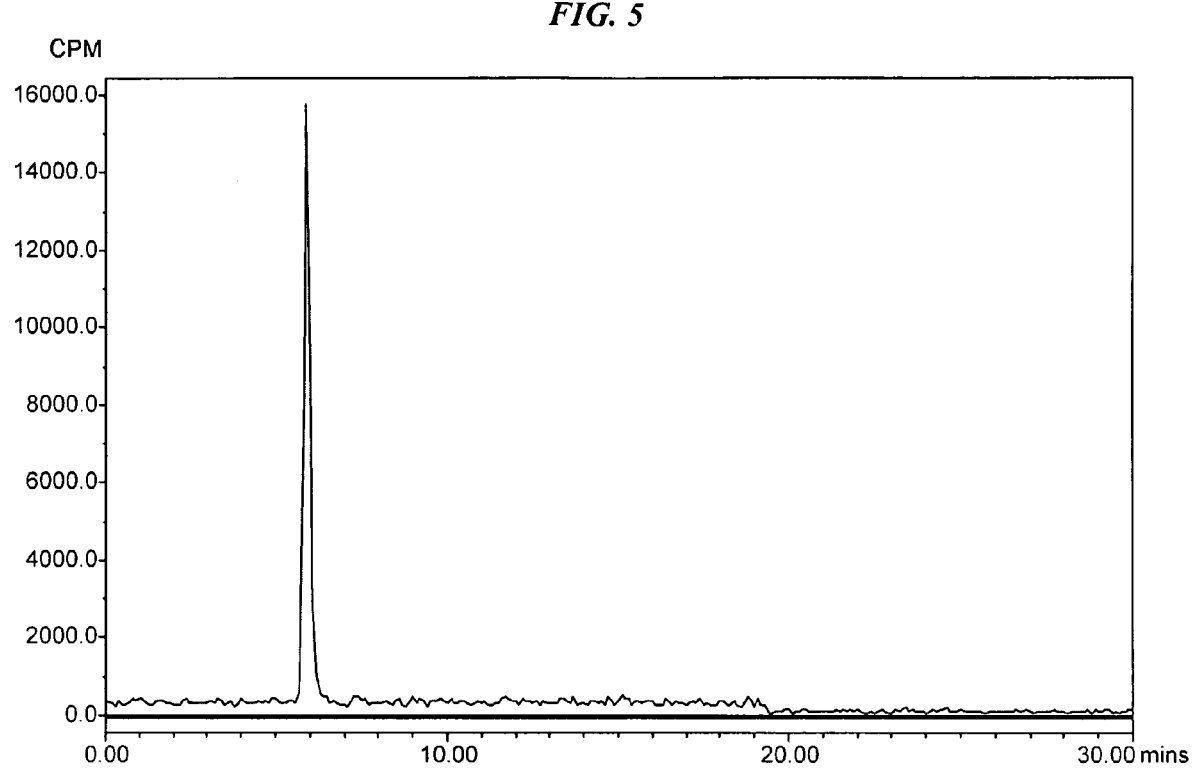
FIG. 5. Analysis of α-Hydroxy-4-[$^{18}$F]Fluoro-α-toluenesulfonic Acid by Reverse Phase HPLC and Radiometric Detection. The change in baseline at 20 min was due to movement of samples in the carousel of the auto injector.

Tetrabutyl ammonium chloride, 0.0032 g, was mixed with 50 µL of a 40% sodium bisulfite solution, 2.5 µL ($2.6 \times 10^{-3}$ M) IMP 316 and added to 1060 µCi 4-[$^{18}$F]Fluorobenzaldehyde (HPLC RT 15.5 min, FIG. 5) in 1 mL methanol. The sealed vessel was placed in a 100° C. heating block and the solution was evaporated under a stream of argon (the argon stream effluent was bubbled through a solution of 40% bisulfite to trap any volatilized 4-[$^{18}$F]Fluorobenzaldehyde). The solution was evaporated to obtain 872 µCi (91% recovery, decay corrected) of the dried product, which was fully converted to a new shorter retention time product by reverse phase HPLC (HPLC RT 6.0 min). There was no sign of conjugation to the peptide under the conditions used here but conversion to the bisulfite addition complex appeared to be complete.

4) Peptide Synthesis

The peptides were synthesized on solid phase resins using the Fmoc strategy. The allyloxy carbonyl (Aloc) protecting group was used to protect amino groups, such as those on lysine side chains, for differential protection so that they could be selectively deprotected when desired. Once the lysine side chains had been deprotected the desired substituent could be attached.

5) Conjugation of 4-Fluorobenzaldehyde to Peptides

Optimum Conjugation Conditions for 4-Fluorobenzaldehyde to the Peptides:

The conjugation of cold 4-Fluorobenzaldehyde to the three peptides was examined to compare the reaction and stability of the oxime, hydrazone and thiosemicarbazone linkages.

The influence of pH on the reaction was investigated as well as the effect of different solvents. These reactions generally followed the methods described by Poethko et al. The conjugates were formed, purified by HPLC and confirmed by ESMS. Once the desired solvent and pH profile for the conjugates was found, the conjugations were performed under the optimized conditions with 4-[$^{18}$F]Fluorobenzaldehyde. The retention time of the confirmed conjugates was compared to the retention times of the F-18 labeled conjugates by HPLC (reverse phase and size exclusion HPLC). The F-18 conjugated peptides were mixed with the bispecific antibodies and monitored (radiometric detection) for the expected shift in retention time as the peptide binds to two of the bispecific antibodies by size exclusion HPLC and shifts the activity (~14 min peptide) to a shorter retention time (~9 min peptide antibody complex).

6) Concentration of 4-[$^{18}$F]Fluorobenzaldehyde

The reaction of the peptide with the 4-[$^{18}$F]Fluorobenzaldehyde was dependent on the relative concentrations of the two reagents. If the 4-[$^{18}$F]Fluorobenzaldehyde was dilute then a lot of peptide had to be added to achieve a concentration of the peptide that would drive the reaction to completion. If excess, unreacted, peptide was present in the final product it could fill most of the binding sites on the bispecific antibodies, which are attached to the tumor surface, and block the binding of the F-18 labeled conjugate. If the 4-[$^{18}$F] Fluorobenzaldehyde could be concentrated then that would minimize the amount of peptide needed for the conjugation which would boost the effective specific activity of the labeled peptide. If the effective specific activity was high enough after the conjugation then removal of excess peptide was not necessary. The bisulfite addition complex of 4-[$^{18}$F] Fluorobenzaldehyde was formed quantitatively.

7) Removal of Excess Peptide

The reaction of 4-[$^{18}$F]Fluorobenzaldehyde with IMP 316 as described above produced the conjugated peptide at ~1

Ci/mmol. If that reaction is performed with 1 to 3 Ci of F-18 then the specific activity of the conjugate is sufficient for imaging studies. If it takes a lot more peptide to drive the reaction to completion then it might be necessary to remove excess unreacted peptide to increase the effective specific activity of the conjugate/peptide mixture. It is possible to remove some of the peptide on an ion exchange column. The amount of peptide bound on an ion exchange column may be pH dependent. The cold 4-fluorobenzaldehyde peptide conjugate is made and the amount of peptide retained at different pH's on an ion exchange resin is monitored by HPLC. The process is repeated with the unconjugated peptides to find conditions that selectively remove the peptide in the presence of the conjugate. The peptide conjugate is more hydrophobic than the precursor peptide so it is possible to separate the conjugate from the unreacted peptide on a C-18 Sep-Pak cartridge (Waters Oasis® HLB). Sep-Pak cartridges are available, which contain both hydrophobic and ionic separation selectivities [Waters Oasis® MAX (anions) and MCX (cations)]. It is also feasible to use a column or resin, which contains reactive components such as displaceable halogens, aldehydes or ketones to trap the reactive ends of the excess unreacted peptides. Resins containing displaceable halogens, aldehydes and ketones are available from commercial manufacturers such as Advanced ChemTech (Halogenated resins (SP5022, SC5055), Aldehyde resins SB5007, SP5007, SA577, a ketone resin SA5040).

8) Conjugations of Fluorobenzaldehydes to Peptides

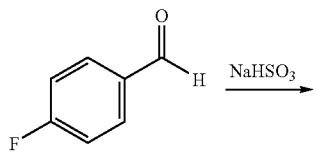

4-Fluorobenzaldehyde bisulfite addition complex

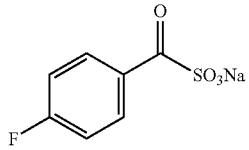

Sodium bisulfite, 1.8552 g ($1.78 \times 10^{-2}$ mol, 217 mol %) was dissolved in 5 mL water and mixed with 1.020 g ($8.22 \times 10^{-3}$ mol, 100 mol %) 4-Fluorobenzaldehyde. The solution warmed slightly and a white precipitate formed. The white precipitate was collected by filtration and washed with 50 mL water. The recovered solid was dried to afford 0.666 g (36% yield) of the desired product. HPLC analysis of the filtrate showed that some of the product was in the filtrate.

$^1$H NMR (DMSO) 5.0 (1 H, doublet), 6.0 (1 H, doublet), 7.06 (2 H, triplet), 7.47 (2 H, multiplet).

$^{13}$C NMR (DMSO) 84.16, 113.6 (d), 129.6 (d), 135.7, 161 (d)

9) Synthesis of IMP 328

The peptide, IMP 327 (101.1 mg, $5.87 \times 10^{-5}$ mol, 100 mol %) was added to a conical glass reaction vial. Acetic acid (117 µL, 1 M) was added and mixture was vortexed to dissolve peptide. The 4-Fluorobenzaldehyde bisulfite addition complex (14.1 mg, $6.18 \times 10^{-5}$ mol, 105 mol %) was added and mixture was again vortexed followed by heating at 100° C. for 5 minutes. RP-HPLC showed that the reaction went to completion. The entire volume was loaded, by dissolving in 2 mL DI H$_2$O, onto a preequilibrated Waters Sunfire Prep C$_{18}$ 5 µm 19×150 mm Column and purified using a flow rate of 25 mL/min and a gradient of 100% A/0% B to 70% A/30% B over 80 minutes. Mobile phase A: 100% DI H$_2$O with 0.1% trifluoroacetic acid. Mobile phase B: 90% acetonitrile/10% DI H$_2$O with 0.1% trifluoroacetic acid. Fractions were lyophilized and analyzed by ESMS. Total peptide recovered was 69.1 mg (64.4% yield).

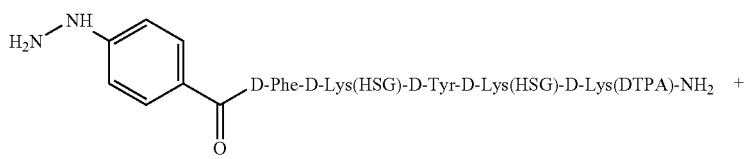

IMP 327, MH$^+$: 1723

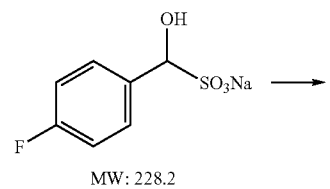

MW: 228.2

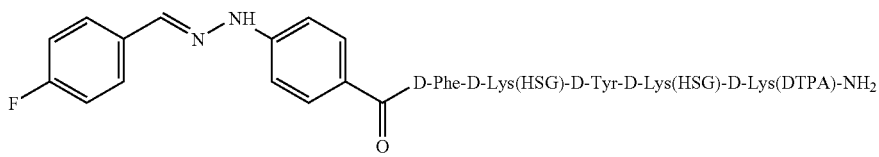

IMP 328, MH$^+$: 1829

10) Synthesis of IMP 330

The peptide, IMP 327 (76.0 mg, $4.41 \times 10^{-5}$ mol, 100 mol %) was added to a conical glass reaction vial. Acetic acid (88 µL, 1 M) was added and mixture was vortexed to dissolve peptide. The 4-Fluorobenzaldehyde bisulfite addition complex (11.1 mg, $4.86 \times 10^{-5}$ mol, 110 mol %) was added and mixture was again vortexed followed by heating at 100° C. for 20 minutes. RPHPLC showed that the reaction went to completion. Sodium cyanoborohydride (16:4 mg, $2.61 \times 10^{-4}$ mol, 592 mol %) was added and the mixture heated again at 100° C. for 20 minutes. The entire volume was loaded, by dissolving in 3 mL DI $H_2O$, onto a preequilibrated Waters Sunfire Prep C18 5 µm 19×150 mm Column and purified using a flow rate of 25 mL/min and a gradient of 100% A/0% B to 70% A/30% B over 80 minutes. Mobile phase A: 100% DI $H_2O$ with 0.1% trifluoroacetic acid. Mobile phase B: 90% acetonitrile/10% DI $H_2O$ with 0.1% trifluoroacetic acid. Fractions were lyophilized and analyzed by ESMS. Total peptide recovered was 9.6 mg (11.9% yield).

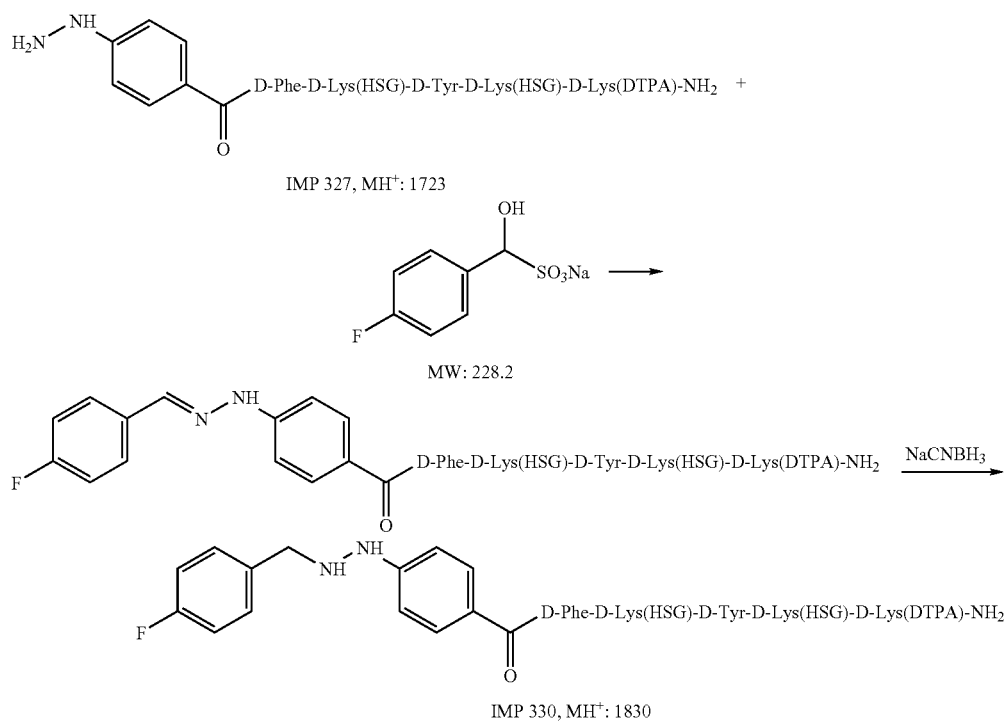

11) Synthesis of IMP 318

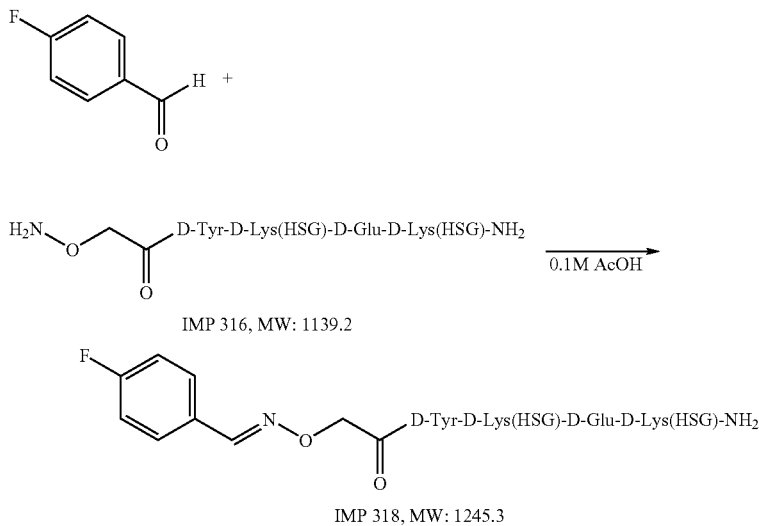

The peptide, IMP 316 (50.0 mg, $4.386\times10^{-5}$ mol, 100 mol %) was placed in a glass conical screw-cap reaction vial. The acetic acid solution (100 µL, 0.1 M) was added and mixed until the peptide dissolved. One equivalent of 4-Fluorobenzaldehyde (4.63 µL, $4.387\times10^{-5}$ mol, 100 mol %) was added to the mixture and vortexed. The reaction mixture was heated at 60° C. for ~30 minutes and monitored by RP-HPLC. The mixture was placed in the freezer overnight, removed next day and heating continued after having added an additional equivalent of 4-Fluorobenzaldehyde. The reaction was nearly complete after heating for most of the day. The mixture was dissolved in 3 mL mobile phase A (100% DI $H_2O$ w/0.1% TFA) and the entire volume loaded onto a preequilibrated Waters Sunfire Prep $C_{18}$ 5 µm 19×150 mm Column and purified using a flow rate of 25 mL/min and a gradient of 100% A/0% B to 70% A/30% B over 80 minutes. Mobile phase A: 100% DI $H_2O$ with 0.1% trifluoroacetic acid. Mobile phase B: 90% Acetonitrile/10% DI $H_2O$ with 0.1% trifluoroacetic acid. Fractions were lyophilized and analyzed by ESMS. Total peptide recovered was 17.0 mg (31.1% yield).

12) Synthesis of IMP 320

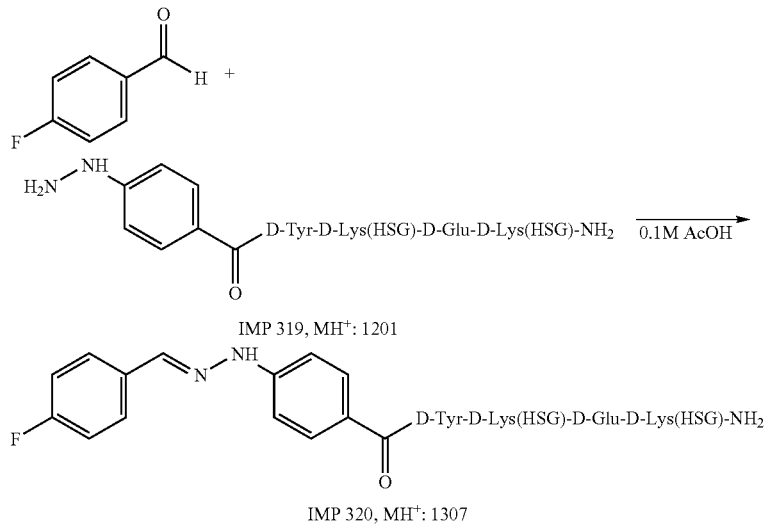

The peptide IMP 319 (68.6 mg, $5.715\times10^{-5}$ mol, 100 mol %) was placed into a glass conical screw-cap reaction vial. Acetic acid (100 µL, 0.1 M) was added and mixed until dissolved. Added one equivalent of 4-Fluorobenzaldehyde (6.63 µL, $6.283\times10^{-5}$ mol, 110 mol %) to mixture and vortexed. Heated at 60° C. for ~20 minutes and monitored by RP-HPLC. The reaction appeared to have gone to completion after ~40 minutes. The mixture was placed in a freezer overnight. It was removed the next day and allowed to warm to room temperature. After dissolving in 2 mL DI $H_2O$ the entire volume was loaded onto a preequilibrated Waters Sunfire Prep $C_{18}$ 5 µm 19×150 mm Column and purified using a flow rate of 25 mL/min and a gradient of 100% A/0% B to 70% A/30% B over 80 minutes. Mobile phase A: 100% DI $H_2O$ with 0.1% trifluoroacetic acid. Mobile phase B: 90% Acetonitrile/10% DI $H_2O$ with 0.1% trifluoroacetic acid. Fractions were lyophilized and analyzed by ESMS. Total peptide recovered was 54.1 mg (72.4% yield).

13) Synthesis of IMP 322

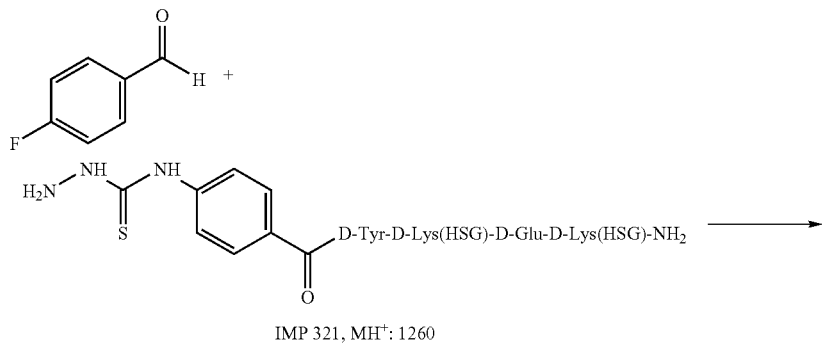

-continued

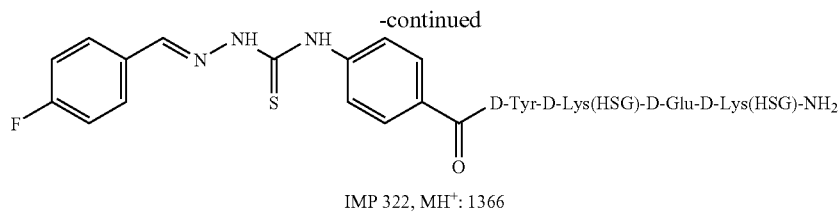

IMP 322, MH+: 1366

The peptide IMP 321 (31.2 mg, 2.477×10$^{-5}$ mol, 100 mol %) was placed into a glass conical screw-cap reaction vial. Acetic acid solution (100 µL, 0.1 M) was added and mixed until the peptide dissolved. One equivalent of 4-Fluorobenzaldehyde (2.88 µL, 2.729×10$^{-5}$ mol, 110 mol %) was added to the reaction mixture and vortexed. The mixture was heated at 60° C. for ~20 minutes and monitored by RP-HPLC. The reaction appeared to have gone to approximately 90% completion after 15 minutes and to completion after ~30 minutes. The mixture was dissolved in 2 mL DI H$_2$O and the entire volume loaded onto a preequilibrated Waters Sunfire Prep C$_{18}$ 5 µm 19×150 mm Column and purified using a flow rate of 25 mL/min and a gradient of 100% A/0% B to 70% A/30% B over 80 minutes. Mobile phase A: 100% DI H$_2$O with 0.1% trifluoroacetic acid. Mobile phase B: 90% acetonitrile/10% DI H$_2$O with 0.1% trifluoroacetic acid. Fractions were lyophilized and analyzed by ESMS. Total peptide recovered was 21.8 mg (64.4% yield).

14) Imaging of Diseased Tissue in Nude Mice

A humanized MN-14 IgG antibody is prepared as described in U.S. Pat. No. 6,676,924. $^{18}$F-labeled bisulfite addition complex is prepared as described in Example 8 and is linked to the humanized MN-14 IgG by reductive amination with sodium cyanoborohydride using standard techniques (see, e.g., Gray, 1978, Meth. Enzymol. 50:155-160.). Alternatively, an antibody or antibody fragment is directly labeled with [$^{18}$F]Fluorobenzaldehyde in the presence of hydroxylamine, thiosemicarbazide or hydrazine. Gel-permeation column chromatography is used to separated the 4-[$^{18}$F]Fluorobenzaldehyde/hMN-14 immunoconjugate from unconjugated 4-[$^{18}$F]Fluorobenzaldehyde bisulfite addition complex. The 4-[$^{18}$F]Fluorobenzaldehyde/hMN-14 immunoconjugate is used to localize human colon cancer tissue in nude mice. At 4-5 weeks female athymic mice (nu/nu, Harlan, Indianapolis, Ind.) are injected s.c. with 0.2 ml of a 10% suspension of LS174T human colon adenocarcinoma prepared from a xenograft serially propagated in an athymic mouse (Sharkey et al., Cancer Res., 50: 828-34 (1990)). After waiting 2 weeks for tumor development, the mice are injected i.v. with 20 µCi of 4-[$^{18}$F]Fluorobenzaldehyde/hMN-14 immunoconjugate. Tumor tissue is imaged by PET imaging, using standard $^{18}$F detection methods. The tumors are detected as hot spots of F-18 distribution against a low-level background of F-18.

15) Imaging of Diseased Tissue with Bispecific Antibodies

A humanized bispecific MN-14×679 F(ab')$_2$ antibody fragment is prepared as described in U.S. Pat. Nos. 6,962,702 and 7,011,816 (the Examples sections of which are incorporated herein by reference). A 67-year old human male with a suspected colon cancer is injected i.v. with the bispecific humanized MN-14×679 F(ab')$_2$ (10$^{-9}$ mol). After allowing 24 hours for free antibody fragment to clear from the circulation, the subject is injected with F-18 labeled IMP 322 (100 µCi), whose HSG moieties bind to the 679 Fab'. The presence of a CEA expressing tumor is confirmed by PET imaging of the localized F-18 label and the subject is diagnosed with colon cancer.

What is claimed is:

1. A method of radiolabeling a protein or peptide comprising a nucleophilic nitrogen atom, comprising:
    a) contacting said protein or peptide with a bisulfate addition complex of [$^{18}$F]Fluorobenzaldehyde; and
    b) forming a carbon-nitrogen double bond between said nucleophilic nitrogen atom and said [$^{18}$F]Fluorobenzaldehyde.

2. The method of claim 1, wherein said nucleophilic nitrogen atom is part of a moiety selected from the group consisting of a primary amine, a secondary amine, a hydroxylamine, a thiosemicarbazide and a hydrazine.

3. The method of claim 1, further comprising reducing said double bond with a reducing agent.

4. The method of claim 1, wherein the protein or peptide is an antibody or antibody fragment.

5. The method of claim 1, wherein the bisulfite addition complex of [$^{18}$F]Fluorobenzaldehyde is formed by reacting 4-[$^{18}$F]fluorobenzaldehyde with sodium bisulfite.

6. The method of claim 1, wherein a solution containing the bisulfite addition complex of [$^{18}$F]Fluorobenzaldehyde is evaporated to dryness to concentrate the bisulfite addition complex before it is contacted with the protein or peptide.

7. The method of claim 1, wherein the bisulfite addition complex of [$^{18}$F]Fluorobenzaldehyde is contacted with the protein or peptide in an aqueous medium to form a mixture.

8. The method of claim 7, wherein the mixture is heated.

9. The method of claim 8, wherein the mixture is heated to 100° C.

10. The method of claim 3, wherein the reducing agent is sodium cyanoborohydride.

11. The method of claim 1, wherein the peptide is selected from the group consisting of IMP 286, IMP 316, IMP 318, IMP 319, IMP 320, IMP 321, IMP 322, IMP 327, IMP 328 and IMP 330.

\* \* \* \* \*